(12) United States Patent
Shang

(10) Patent No.: US 10,639,496 B2
(45) Date of Patent: May 5, 2020

(54) BLOOD VESSEL OPTICAL FIBER GUIDE WIRE

(71) Applicant: Hua Shang, Nanjing (CN)

(72) Inventor: Hua Shang, Nanjing (CN)

(\*) Notice: Subject to any disclaimer, the term of this patent is extended or adjusted under 35 U.S.C. 154(b) by 75 days.

(21) Appl. No.: 15/605,240

(22) Filed: May 25, 2017

(65) Prior Publication Data

US 2018/0178027 A1   Jun. 28, 2018

Related U.S. Application Data

(63) Continuation of application No. PCT/CN2017/077668, filed on Mar. 22, 2017.

(30) Foreign Application Priority Data

Dec. 28, 2016   (CN) .......................... 2016 1 1234625

(51) Int. Cl.
*A61N 5/00* (2006.01)
*A61N 5/06* (2006.01)
(Continued)

(52) U.S. Cl.
CPC ........... *A61N 5/0601* (2013.01); *A61N 5/062* (2013.01); *A61N 2005/0602* (2013.01);
(Continued)

(58) Field of Classification Search
CPC .... A61N 5/0601; A61N 5/062; G02B 6/4402; G02B 6/4415
(Continued)

(56) References Cited

U.S. PATENT DOCUMENTS

| 5,330,465 A | 7/1994 | Doiron et al. |
| 7,252,677 B2 * | 8/2007 | Burwell ............... A61N 5/0601 606/13 |

(Continued)

FOREIGN PATENT DOCUMENTS

| CN | 101622030 A | 1/2010 |
| CN | 203244695 U | 10/2013 |

(Continued)

OTHER PUBLICATIONS

Sep. 1, 2017 International Search Report and Written Opinion issued in Patent Application No. PCT/CN2017/077668.

*Primary Examiner* — Scott M. Getzow
*Assistant Examiner* — Sana Sahand
(74) *Attorney, Agent, or Firm* — Hauptman Ham, LLP

(57) ABSTRACT

A blood vessel optical fiber guide wire includes at least one of optical fiber core wire, a wire wrapping layer and a hydrophilic coating capable of improving compatibility with body liquids and reducing the resistance. The optical fiber core wire is disposed in a core of the optical fiber guide wire. The wire wrapping layer is formed from at least one of winding wire or winding sheet wrapping outside of the optical fiber core wire. The hydrophilic coating is coated outside of the wire wrapping layer. The optical fiber guide wire may enter a predetermined position in artery blood vessel of human body. The light can be guided into and/or guided out of a location of lesion so as to achieve the photodynamic treatment of diseases such as tumor in vivo. The need to diagnosis and treatment in the field including biology and medical treatment can be met.

9 Claims, 4 Drawing Sheets

(51) Int. Cl.
*G02B 6/44* (2006.01)
*G02B 6/36* (2006.01)

(52) U.S. Cl.
CPC ...... *A61N 2005/063* (2013.01); *G02B 6/3624* (2013.01); *G02B 6/4402* (2013.01); *G02B 6/443* (2013.01); *G02B 6/4415* (2013.01)

(58) Field of Classification Search
USPC .......................................................... 607/88
See application file for complete search history.

(56) References Cited

U.S. PATENT DOCUMENTS

| | | | | |
|---|---|---|---|---|
| 7,532,920 | B1 * | 5/2009 | Ainsworth | A61B 5/02007 600/341 |
| 9,925,389 | B1 * | 3/2018 | Shang | A61N 5/062 |
| 2003/0009157 | A1 * | 1/2003 | Levine | A61B 18/26 606/7 |
| 2005/0104059 | A1 * | 5/2005 | Friedman | A61M 25/1011 257/40 |
| 2006/0217793 | A1 * | 9/2006 | Costello | A61N 1/056 607/122 |
| 2008/0033519 | A1 * | 2/2008 | Burwell | A61N 5/0601 607/122 |
| 2009/0275931 | A1 * | 11/2009 | Markus | A61B 18/24 606/15 |
| 2010/0268151 | A1 * | 10/2010 | Mauge | A61M 27/006 604/21 |
| 2010/0312312 | A1 * | 12/2010 | Jones | A61N 5/062 607/88 |
| 2011/0040357 | A1 * | 2/2011 | Arai | A61N 5/0601 607/88 |
| 2013/0006118 | A1 * | 1/2013 | Pan | A61N 5/0616 600/476 |
| 2013/0006119 | A1 * | 1/2013 | Pan | A61B 5/0059 600/476 |
| 2014/0276355 | A1 * | 9/2014 | Tardy | A61N 5/0622 604/20 |
| 2016/0089547 | A1 * | 3/2016 | Shimizu | A61N 5/0625 607/89 |
| 2016/0151639 | A1 * | 6/2016 | Scharf | A61N 5/0601 607/92 |
| 2017/0173349 | A1 * | 6/2017 | Pfleiderer | A61N 5/0622 |
| 2017/0246472 | A1 * | 8/2017 | Chen | A61N 5/062 |
| 2018/0154152 | A1 * | 6/2018 | Chabrol | A61N 1/36067 |

FOREIGN PATENT DOCUMENTS

| | | | |
|---|---|---|---|
| CN | 103480077 A | 1/2014 | |
| CN | 103861195 A | 6/2014 | |
| CN | 205287198 U | 6/2016 | |
| EP | 0669820 B1 * | 4/1997 | ........... A61B 5/0084 |
| WO | WO-2008096561 A1 * | 8/2008 | ........... A61B 18/24 |

* cited by examiner

BLOOD VESSEL OPTICAL FIBER GUIDE WIRE

TECHNICAL FIELD

The present application relates to the technical field of medical equipment, specifically to a blood vessel optical fiber guide wire that can enter human body through artery blood vessel and achieve the photodynamic treatment of diseases such as tumor.

BACKGROUND OF THE INVENTION

Currently, Seldinger artery encheiresis is very mature, It can be used under the guidance of clinic imaging medicine (X-ray, CT, MR, B-us, etc.) for diagnostic radiography and treatment. Through percutaneous vascular approach or inherent orifices and cavities of human body, fine devices such as special catheters and wires are inserted into the location of lesion. Metal guide wire-percutaneous vascular approach is used in this technology to enter blood vessel and reach the location of lesion, which is simple with less injure, without the suture of blood vessels, and can completely replace conventional surgery exploring blood vessels. It is the basis of the interventional radiology, and has achieved good results on embolism of tumor and drug perfusion, artery irradiation, prevention of radioactive injury, chemotherapy, pre-operative embolization of tumor blood vessel, perfusion of drugs in blood vessel and ethyl alcohol, etc. However, due to the limitation of treatment, the disease mainly consists of tissue is chemia and hypoxia, and further necrosis caused by embolism or the growth of cells inhibited by perfusing drugs, organ morphology changed by releasably implanting medical equipment, cannot guide the light into blood vessels and body or out of blood vessels and body.

Compared with common means including surgery, chemotherapy and radiotherapy in the art, the photodynamic therapy of tumor possess has several advantages, such as less injury, less toxicity, better targeting and improved feasibility. However, the irradiation is just limited to the body surface or larger orifices and cavities. Due to limitation of mechanism of laser emitting and medicinal properties of photosensitizers, the range of photodynamic action is just in several millimeters, which greatly limits its application to the medical field. Currently, the light cannot be guided into blood vessel for diagnosis and treatment. In the present application, winding wire and hydrophilic coating wrapping optical fiber are used to form operable blood vessel optical fiber guide wires with different length and diameter to enter blood vessels. The light is guided into and out of blood vessels adjacent to the location of lesion through optical fiber core wires, to meet the needs in the fields of biology and medical treatment for guiding into and out of blood vessels, which play the double role of diagnosis and treatment.

SUMMARY OF THE INVENTION

Aiming at the defects of Seldinger artery encheiresis, such as catheter and guide wire which cannot transmit light energy, as well as photodynamic treatment which cannot reach the location of lesion in vivo, the present application provides a blood vessel optical fiber guide wire, which can enter the body through blood vessels, and guide the light into and out of the location of lesion, thereby solving the problems, such as the guide wire which cannot transmit the light and photodynamic treatment which cannot arrive the location of lesion in vivo.

To achieve the above-mentioned object, the present application provides a blood vessel optical fiber guide wire, comprising at least one of optical fiber core wire for transmitting the light, which is disposed in a core of the optical fiber guide wire;

a wire wrapping layer, which is formed from at least one of winding wire wrapping outside of the optical fiber core wire; and a hydrophilic coating capable of improving compatibility with body liquids and reducing the resistance, which is coated outside of the wire wrapping layer.

Further, the optical fiber core wire comprises fiber core and a clad layer coated outside of each of the fiber core; the light conductivity of the clad layer is lower than that of the fiber core.

Further, the optical fiber guide wire preferably comprises more than two optical fiber core wires comprising a first fiber core guiding into the light and a second fiber core guiding out of the light.

Further, the fiber core is a single mode fiber core or a multimode fiber core.

Further, the material of the fiber core is at least one selected from the group consisting of quartz fiber core, polymer fiber core or and metal hollow fiber core.

Further, one or more metal/polymer guide wires in parallel with the fiber core can be incorporated into the fiber core to improve the strength.

Further, the hydrophilic coating is made from chemically stable materials.

Further, materials of the hydrophilic coating comprise polytetrafluoroethylene, silicone rubber, polyethylene, polyvinyl chloride, fluorine carbon polymer and polyurethane.

Further, the winding wire comprises metal winding and non-metal winding wire.

Further, the winding wire comprises at least one selected from the group consisting of stainless steel winding wire, synthetic fiber winding wire, carbon fiber winding wire, platinum winding wire and titanium alloy winding wire.

Further, the winding wire is wrapped closely outside of the optical fiber core wire to restrain the light in the optical fiber core wire.

Further, a light guide part is disposed at the head portion of the end that the optical fiber guide wire is guided into the blood vessel;

the light guide part comprises a light transmitting part and a micro lens disposed at the top of the light transmitting part and capable of guiding the light out of/guiding the light into the fiber core;

several light guiding holes are disposed on the light transmitting part passing through the hydrophilic coating and wire wrapping layer and being perpendicular to the optical fiber core wire.

Further, the length of the light transmitting part is generally in the range of 1 to 4 cm, preferably in the range of 2 to 3 cm.

Further, the micro lens can be a structure of outward hemisphere.

Further, the other end of the optical fiber guide wire is connected with a coupling device; and an operating arm is disposed at the light coupling device.

The diameter of the optical fiber guide wire is in the range of 90 μm to 2000 μm, preferably in the range of 100 μm-1000 μm.

The length of the optical fiber guide wire is in the range of 1.5 to 2 m.

The present application possesses the following advantageous effects:

The optical fiber guide wire of the present application can enter the body through blood vessels. That is, the optical fiber guide wire arrives at a predetermined the location of lesion in blood vessels. The light is guided into and out of the location of lesion such that a treatment and diagnosis can be achieved. For example, the photosensitizer drug may work.

Specifically, a hydrophilic coating disposed at the outermost layer of in the optical fiber guide wire may improve the blood compatibility and reduce the resistance of blood. The specific disposition of winding wire in the wire wrapping layer may improve the tenacity and strength to facilitate entering human body of the optical fiber guide wire. Its specific wrapping pattern may help for entering human body. Incorporating of one or more metal/polymer guide wires into fiber core may also improve its strength. Thus, optical fiber guide wire may enter human body easily. The specific structure of the light transmitting part is helpful for the treatment. The micro lens is also disposed to reduce resistance to the optical fiber guide wire in blood vessel. The operating arm is disposed to facilitate the optical fiber guide wire arrive at the location of lesion in blood vessels of human body.

10. optical fiber guide wire; 11. fiber core; 12. clad layer; 13. wire wrapping layer; 14. hydrophilic coating; 15. micro lens; 16. light guiding hole; 20. light guide part; 30. light coupling device; 131. winding wire or winding sheet.

DETAILED DESCRIPTION OF THE INVENTION

The technical solutions of embodiments of the present application are described clearly and completely as follows. Obviously, the described embodiments are just some not all embodiments of the present application. The protection scope of the present application is not intended to be limited by embodiments of the present application provided below, but just represent selected embodiments of the present application. Based on embodiments of the present application, other embodiments that can be obtained by those skilled in the art without paying any creative work belong to the protection scope of the present application.

Embodiment 1

Figure 1:
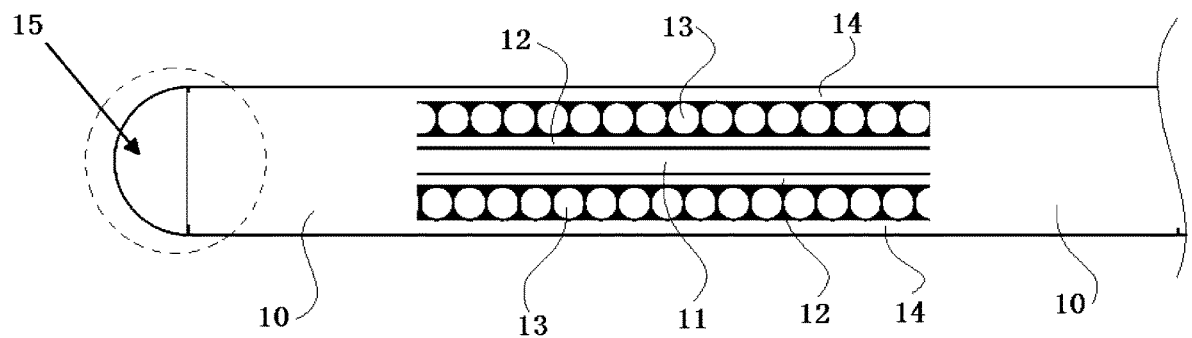
FIG. 1 is a schematic diagram of parts of optical fiber guide wire of an example of the present application.
Figure 2:
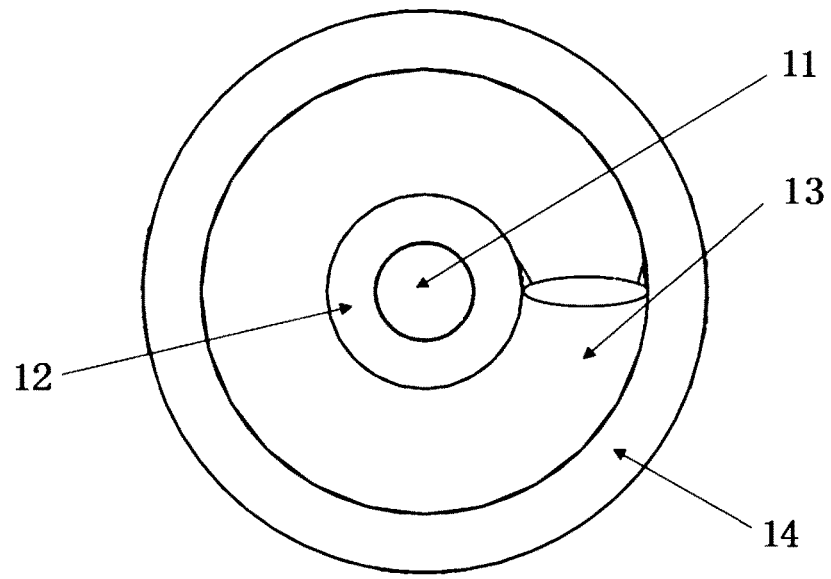
FIG. 2 is a cross section schematic diagram of an optical fiber guide wire of an example of the present application.

As shown in FIG. 1 and FIG. 2, a blood vessel optical fiber guide wire is provided. The optical fiber guide wire 10 comprises a optical fiber core wire, a wire wrapping layer 13 wrapping outside of the optical fiber core wire and a hydrophilic coating 14 coated outside of the wire wrapping layer 13.

The optical fiber core wire is disposed in a core of the optical fiber guide wire 10. The optical fiber core wire comprises a fiber core 11 for transmitting the light (that is, an optical fiber) and a clad layer 12 coated outside of the fiber core 11. The fiber core 11 is a single mode fiber core or multimode fiber core. The material of the fiber core 11 is at least one selected from the group consisting of quartz fiber core, polymer fiber core and metal hollow fiber core. The light conductivity of the clad layer 12 is less than that of the fiber core 11. Thus, the clad layer 12 may restrain the light in the fiber core 11.

The wire wrapping layer 13 is formed from at least one of winding wire or winding sheet 131 wrapping outside of the optical fiber core wire. The winding wire 131 is wrapped outside of the optical fiber core wire to improve its tenacity and strength. Generally, the winding wire 131 is closely warped outside of the optical fiber core wire to restrain the light in the optical fiber core wire.

The hydrophilic coating 14 is disposed to improve body liquid compatibility and reduce the resistance of the optical fiber guide wire 10 in body. For example, the blood compatibility may be improved and the resistance in blood may be reduced. The hydrophilic coating 14 can be made from a chemically stable material.

The material of hydrophilic coating 14 includes but not limited to polytetrafluoroethylene, silicone rubber, polyethylene, polyvinyl chloride, fluorine carbon polymer and polyurethane. Any one or more of the above can be used to form the hydrophilic coating 14. The hydrophilic coating 14 may be disposed outside of the wire wrapping layer 13 by coating film, coating or thermal shrinkage.

Figure 3:
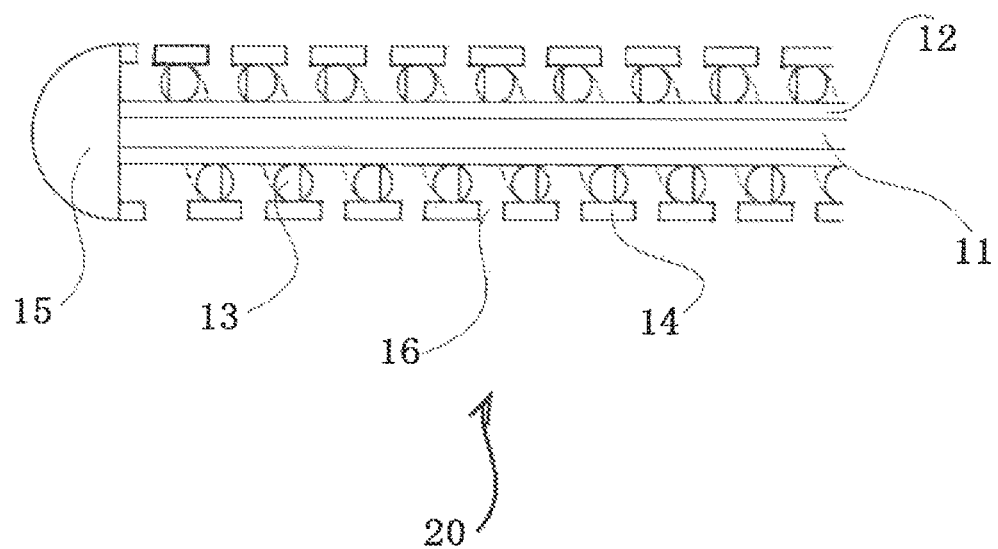
FIG. 3 is a cross sectional views of the inside of dash line in FIG. 1.

As shown in FIG. 3, a light guide part 20 is disposed at the head portion of the end of the optical fiber guide wire 10 for entering blood vessel of human body. The light guide part 20 comprises a light transmitting part and a micro lens 15 disposed at the top of the light transmitting part (that is, the top of the optical fiber guide wire 10) and capable of guiding the light into or out of the fiber core 11. The optical fiber core wire extends from the main body of the optical fiber guide wire 10 to the light transmitting part. The light transmitted in the optical fiber core wire is converged to the optical fiber guide wire 10 from micro lens 15. The location needed is irradiated. Several light guiding holes 16 are disposed on the light transmitting part passing through the hydrophilic coating 14 and wire wrapping layer 13 and being perpendicular to the optical fiber core wire. The optical fiber core wires are exposed through these holes. The optical fiber core wire can be seen directly through these holes. Small part of light in fiber core 11 will go through the clad layer 12 and being guided out of the light guiding hole 16. The length of the light transmitting part is in the range of 1 to 4 cm, preferably in the range of 2 to 3 cm, which is helpful for treatment and advance of the optical fiber guide wire 10.

Figure 7:
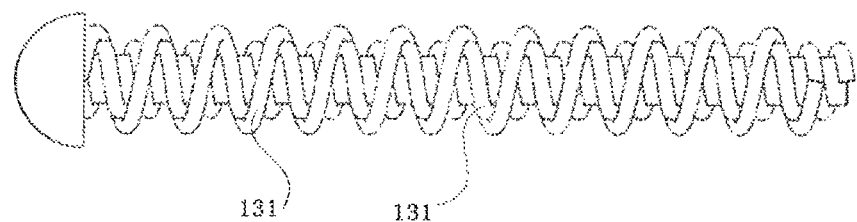
FIG. 7 is a schematic diagram of wrapping pattern of several winding wires in optical fiber guide wire of an example of the present application.

The light guiding hole 16 in the above light transmitting part can be formed by wrapping winding wire 131, for example, as the winding wire 131 is not tightly wrapped, as shown in FIG. 7. That is, gaps are reserved between the adjacent winding wires 131. The hydrophilic coating 14 is directly coated on the winding wire 131. The gaps between the winding wires 131 form the light guiding hole 16.

Other parts of the optical fiber guide wire 10 than the light transmitting part are preferably winding wire 131 wrapped closely to ensure the strength of the optical fiber guide wire 10 and no leaked light.

The micro lens 15 is capable of converging light or heat easily in a circular or hemispherical configuration, etc. Further, the micro lens 15 also reduces the resistance of the optical fiber guide wire 10 when passing through blood vessels, certainly, the micro lens 15 can be in other configuration.

Figure 4:
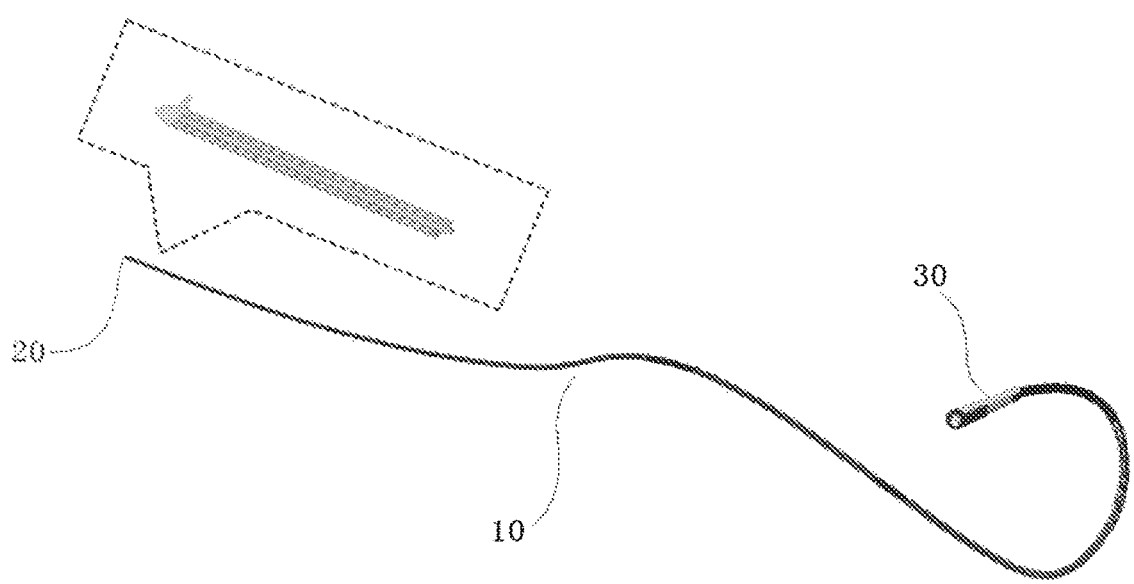
FIG. 4 is a schematic diagram of the total structure of the optical fiber guide wire of an example of the present application.

As shown in FIG. 4, the other end of the optical fiber guide wire 10, that is the end left outside of the body for operating by the user is connected to a coupling device 30. Preferably, the coupling device 30 may rotate. A operable operating arm is disposed outside of the light coupling device 30. The optical fiber guide wire 10 enters a predetermined position in blood vessel by rotation. That is, when the optical fiber guide wire 10 is rotated into blood vessels to a location of lesion for irradiation, the light may be guided into or out of the optical fiber guide wire 10 to play roles of diagnosis and treatment.

As a further preferred embodiment, one or more metal/polymer guide wire in parallel with the fiber core 11 can be incorporated into the fiber core 11 to improve the strength.

Embodiment 2

Figure 5:
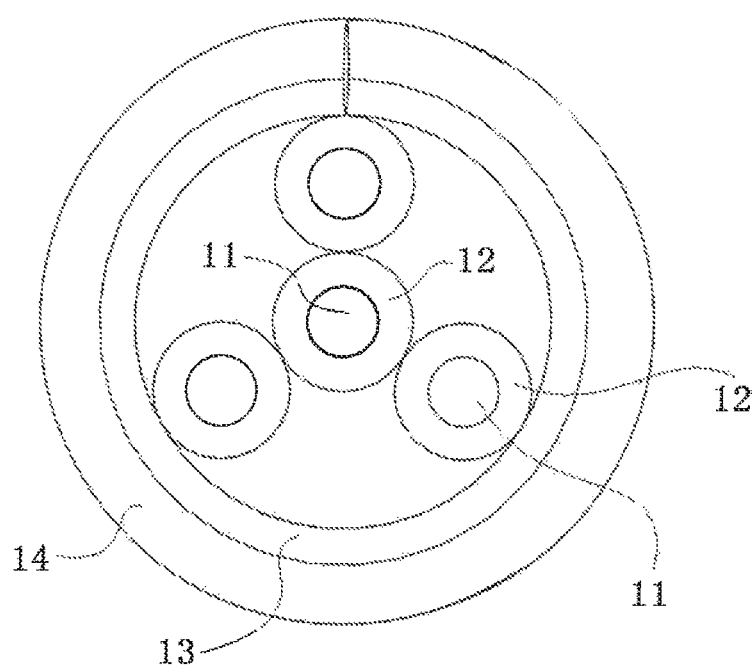
FIG. 5 is a cross section schematic diagram of optical fiber guide wire in another example of the present application.

As shown in FIG. 5, the number of optical fiber core wires in example 1 can be two or greater. The optical fiber core wires can be disposed in a core of optical fiber guide wire 10 in parallel. The optical fiber core wire comprises a fiber core 11 and a clad layer 12 coated outside of each fiber core 11. The winding wire of wire wrapping layer 13 is wrapped outside of all optical fiber core wires to improve their tenacity and strength. The light conductivity of the clad layer 12 is less than that of the fiber core 11. Therefore, the clad layer 12 may restrain the light in the fiber core 11.

If optical fiber guide wire 10 comprises several fiber cores 11, the fiber core 11 may comprise a first fiber core guiding into the light and a second fiber core guiding out of the light. That is, in case of several fiber cores 11, one or more fiber cores can be used to guide into the light. Simultaneously, one or more fiber cores can be used to guide out of the light. The fiber core guiding into the light may transmit the light out of blood vessel after the light effecting. A computer can be used to analyze the data such as spectrum of light guided out of the fiber cores to determine the treatment or diseases, etc. Then, the appropriate therapies can be used for treating.

Other configurations are the same as those in Example 1, so their description is omitted herein.

Embodiment 3

Figure 6:
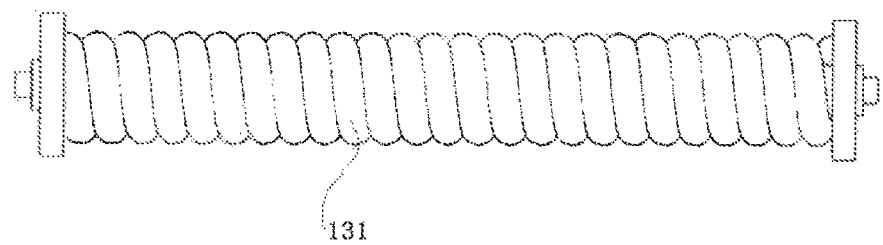
FIG. 6 is a schematic diagram of the winding wire wrapping pattern of the optical fiber guide wire of an example of the present application.
Figure 8:
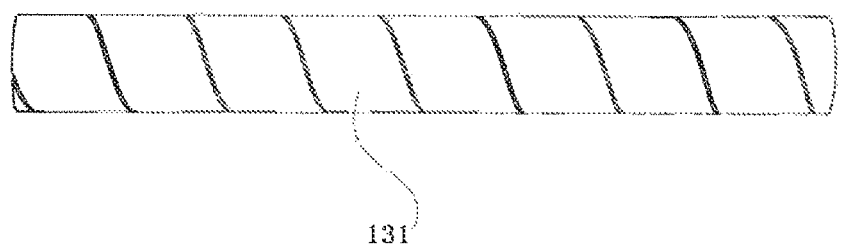
FIG. 8 is a schematic diagram of wrapping pattern of the winding sheet of the optical fiber guide wire of an example of the present application.

Based on Embodiment 1, as shown in FIG. 6, the wrapping pattern of the winding wire 131 can be achieved by closely encircling the outside of the optical fiber core wire through one metal or non-metal winding wire with a diameter of tens of micron. As shown in FIG. 7, winding wire 131 can also wrap the optical fiber core wire through two winding wires 131. Two winding wires 131 can be wove to form two layers of winding wire 131, forming the wire wrapping layer 13. Certainly, more metal/non-metal winding wires can be used. As shown in FIG. 8, the above-mentioned winding wire 131 can also be a winding sheet. The winding sheet is wrapped outside of the optical fiber core wire. The winding sheet can also be metal tube or films. A soft structure wrapped, such as hypotube can be formed by cutting. Certainly, the wrapping pattern of winding wire or winding sheet 131 is not limited to the above.

The material of the winding wire or winding sheet 131 includes metal winding wire and/or non-metal winding wire. Specifically, materials of winding wire or winding sheet 131 includes but not limited to any one of stainless steel winding wire, synthetic fiber winding wire, carbon fiber winding wire, platinum winding wire and titanium alloy winding wire, or combination thereof.

In summary, a winding wire 131 of the wire wrapping layer 13 can be one or more layers. The materials can be metal and/or non-metal material. The structure of the winding wire 131 is threadiness, sheet or tubular. The wrapping method can be coating, winding or knitting.

Certainly, in this example, the specification of the winding wire 131 can be selected according to the actual needs. For example, a larger or smaller winding wire 131 can be selected.

Embodiment 4

In photodynamic tumor treatment, if a liver tumor is treated by the interventional treatment, it needs to enter blood vessels in liver tumor. The optical fiber guide wire 10 is coupled with a laser emitter through a coupling device 30. An end of the optical fiber guide wire 10 at which the micro lens 15 is disposed enters blood vessels percutaneously. Under the guidance of clinic imaging, the optical fiber guide wire 10 is slowly rotated into blood vessels until to the location of lesion to irradiate. After opening the laser emitter, the laser light guided into by the optical fiber guide wire irradiates tumor into which a photo sensitizer has been injected. Therefore, the photo sensitizer reacts in the tumor and produces singlet oxygen to cause the necrosis and apoptosis of the tumor achieving the target of tumor treatment.

Specifically, the diameter of the optical fiber guide wire 10 in the present application is only hundreds of microns. Generally, the largest diameter is about 2 mm. The smallest diameter is only about 100 μm. Therefore, the interventional treatment in human body can be achieved through blood vessels. The length of the optical fiber guide wire 10 is generally in the range of 1.5 to 2 m. Due to this length, the light source can be transmitted to any locations of lesion in human body, with 0.4-1 m remain outside of the body.

During the specific use, the number of semiconductor laser 4 can be selected according to the actual needs. A general range of wavelength can be adjusted by selecting the number of semiconductor laser 4. The precise wavelength can be selected according to the corresponding relationship between the wavelength and temperature. The adjustment of precise range of wavelength can be achieved by adjusting the temperature. Specifically, the temperature of semiconductor chilling plate 5 can be converted into the wavelength to facilitate user's adjustment.

The above is just some preferable embodiments of the present application, rather than the limitation to the present application. For those skilled in the art, various of modifications and changes could be made in the present application. Any modifications, equivalents, and improvements without departing from the spirit and principle of the present application should fall into the protection scope of the present application.

The invention claimed is:

1. A blood vessel optical fiber guide wire comprising:
   at least one optical fiber core wire for transmitting light, which is disposed in a core of the optical fiber guide wire;
   a wire wrapping layer, which is formed from at least two winding wires wrapping an outside of the optical fiber core wire; and
   a hydrophilic coating capable of improving compatibility with body liquids and reducing resistance, which is coated on an outside of the wire wrapping layer, wherein
   a light guide part is disposed at a head portion of the end that the optical fiber guide wire is guided into the blood vessel,
   the light guide part comprises a light transmitting part and a micro lens disposed at the head portion of the light transmitting part and capable of guiding the light out of and guiding the light into the fiber core,
   several light guiding holes are disposed on the light transmitting part passing through the hydrophilic coating and wire wrapping layer and being perpendicular to the optical fiber core wire,
   the several light guiding holes are formed by gaps in the at least one two winding wire, and wires,
   the optical fiber core wire comprises a fiber core and a clad layer coated on an outside the fiber core and in contact between the fiber core and the at least one two winding wires to guide at least some of the light out through the several light guiding holes, said cladding layer having at least some light conductivity,
   the clad layer is coated over substantially the entire length of the fiber core, and
   the light guiding holes in the light transmitting part are formed by wrapping the at least two winding wires such that gaps are reserved between adjacent portions of the at least two winding wires, and the length of the light transmitting part is in a range of 1 cm to 4 cm.

2. The blood vessel optical fiber guide wire according to claim 1, wherein the light conductivity of the clad layer is lower than that of the fiber core.

3. The blood vessel optical fiber guide wire according to claim 1, wherein one or more metal/polymer guide wires in parallel with the fiber core are incorporated into the fiber core to improve the strength.

4. The blood vessel optical fiber guide wire according to claim 1, wherein
   the optical fiber guide wire comprises more than two optical fiber core wires comprising a first fiber core guiding into the light and a second fiber core guiding out of the light;
   the at least two winding wires are wrapped closely on the outside of the optical fiber core wire to restrain the light in the optical fiber core wire.

5. The blood vessel optical fiber guide wire according to claim 1, wherein
   the hydrophilic coating is made from a chemically stable material;
   at least one of the at least two winding wires comprises a metal winding wire and/or a non-metal winding wire;
   the fiber core is a single mode fiber core or a multimode fiber core; and
   the material of the fiber core is at least one selected from the group consisting of quartz fiber core, polymer fiber core or metal hollow fiber core.

6. The blood vessel optical fiber guide wire according to claim 5, wherein
   materials of the hydrophilic coating comprise at least one selected from the group consisting of polytetrafluoroethylene, silicone rubber, polyethylene, polyvinyl chloride, fluorine carbon polymer and polyurethane; and
   at least one of the at least two winding wires comprises at least one selected from the group consisting of stainless steel winding wire, synthetic fiber winding wire, carbon fiber winding wire, platinum winding wire and titanium alloy winding wire.

7. The blood vessel optical fiber guide wire according to claim 1, wherein
   the optical fiber guide wire is left outside of body to connect to a coupling device at the end operated by a user; and
   an operating arm is disposed on the coupling device.

8. The blood vessel optical fiber guide wire according to claim 1, wherein the diameter of the optical fiber guide wire is in the range of 90 μm to 2000 μm.

9. The blood vessel optical fiber guide wire according to claim 8, wherein the length of the optical fiber guide wire is in the range of 1 m to 2 m.

* * * * *